United States Patent [19]

Günther et al.

[11] 4,142,044
[45] Feb. 27, 1979

[54] 4-BENZOXAZOLYL-4'-OXADIAZOLYL STILBENE OPTICAL BRIGHTENERS

[75] Inventors: Dieter Günther, Kelkheim; Rüdiger Erckel; Erich Schinzel, both of Hofheim; Günter Rösch, Bad Soden, all of Fed. Rep. of Germany

[73] Assignee: Hoechst Aktiengesellschaft, Frankfurt am Main, Fed. Rep. of Germany

[21] Appl. No.: 774,396

[22] Filed: Mar. 4, 1977

[30] Foreign Application Priority Data

Mar. 9, 1976 [CH] Switzerland ............................ 2918/76
Oct. 18, 1976 [CH] Switzerland .......................... 13177/76

[51] Int. Cl.$^2$ ............................................ C07D 405/10
[52] U.S. Cl. .................................. 542/464; 252/89 B; 260/307 G; 542/432; 542/435
[58] Field of Search .................... 542/432, 464, 435; 260/307 G; 252/89B

[56] References Cited

U.S. PATENT DOCUMENTS

| | | | |
|---|---|---|---|
| 3,351,591 | 11/1967 | Siegrist et al. ...................... | 542/464 |
| 3,586,673 | 6/1971 | Bloom et al. ....................... | 542/464 |
| 3,689,481 | 9/1972 | Scheuermann et al. ............ | 542/464 X |
| 3,830,848 | 8/1974 | Siegrist ............................. | 542/464 X |
| 3,994,907 | 11/1976 | Domergue .......................... | 260/307 G X |
| 4,003,909 | 1/1977 | Narayanan et al. ............... | 260/307G |
| 4,014,871 | 3/1977 | Kormány et al. .................. | 260/307 G X |
| 4,022,901 | 5/1977 | Narayanan et al. ............... | 260/307 G X |

*Primary Examiner*—Thomas Waltz
*Attorney, Agent, or Firm*—Connolly and Hutz

[57] ABSTRACT

Compounds of the formula

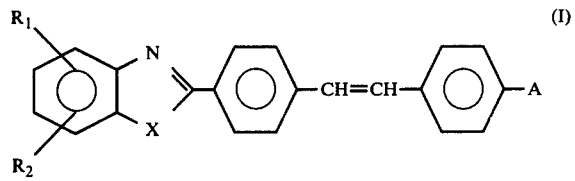

wherein X is O or S, A is a group of the formula

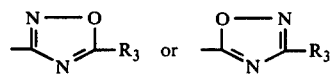

and $R_1$, $R_2$ and $R_3$ are non-chromophorous substituents. They are prepared by reacting a 4'-benzoxa(thia)zolyl-2-stilbene-4-carbonic acid chloride with an amidoxim containing the group $R_3$ or by reacting a 4'-benzoxa(thia)zolyl-2-stilbene-4-amidoxime with an acid chloride containing the group $R_3$.

These compounds are used as optical brighteners.

4 Claims, No Drawings

4-BENZOXAZOLYL-4'-OXADIAZOLYL STILBENE OPTICAL BRIGHTENERS

This invention relates to compounds of the formula

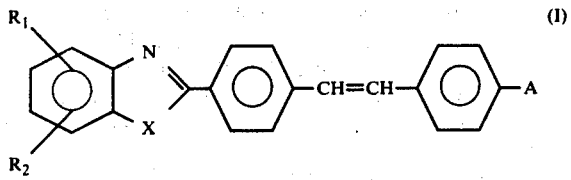

in which X is O or S, $R_1$ and $R_2$, which can be identical or different, are selected from hydrogen, fluorine, chlorine, phenyl, lower alkyl, lower alkoxy, lower dialkylamino, lower trialkylammonium, acylamino and optionally functionally modified carboxy or sulfo radicals, two adjacent radicals $R_1$ and $R_2$ together may represent phenylene, lower alkylene or 1,3-dioxapropylene, and A represents a group of the formula

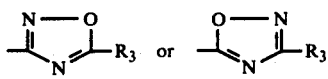

in which $R_3$ represents a straight chain or branched alkyl radical having from 1 to 18 carbon atoms, preferably 1 to 6 carbon atoms, which may be substituted by hydroxy, halogen, lower alkoxy, lower dialkylamino, lower alkylmercapto, chloroaryloxy, aryloxy, arylmercapto, or aryl, in the case of dialkylaminoalkyl the two alkyl groups together possibly forming a morpholine, piperidine or piperazine ring, or $R_3$ represents a group of the formula $-(CH_2CH_2O)_n-R$, wherein n is 1, 2, or 3 and R is hydrogen, lower alkyl, dialkyl-aminoalkoxyalkyl, or alkylthioalkoxyalkyl, the alkyl radicals in the dialkylaminoalkoxyalkyl possibly forming together a piperdine, pyrrolidine, hexamethylene-imine, morpholine or piperazine ring, or $R_3$ stands for a group of the formula $-(CH_2)_m-CH=CH-R$ with m being zero or an integer of from 1 to 5, or a radical of the formula

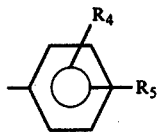

in which $R_4$ and $R_5$, which can be identical or different, are selected from the group of hydrogen, fluorine, chlorine, phenyl, lower alkyl, lower alkoxy, $(C_1-C_4)$-acylamino, or optionally functionally modified carboxy or sulfo groups, two adjacent radicals $R_4$ and $R_5$ may form together a lower alkylene group, a fused benzene ring or a 1,3-dioxapropylene group.

Compounds of formula I in which X, A, $R_1$ and $R_2$ have the aforesaid meanings and $R_3$ represents the following radicals: $(C_1-C_6)$alkyl, $(C_1-C_6)$-chloroalkyl, dimethyl- or diethyl-amino-$(C_1-C_4)$-alkyl, morpholinoethyl, N-$\beta$-piperidino-ethyl, N-$\beta$-(N'-methylpiperazino)-ethyl, benzyl, phenoxy-$(C_1-C_4)$alkyl, chlorophenoxy-$(C_1-C_4)$-alkyl, $(C_1-C_4)$-alkylmercapto-$(C_1-C_4)$alkyl, phenylmercapto-$(C_1-C_4)$-alkyl, phenyl, $(C_1-C_6)$-alkylphenyl, di-$(C_1-C_6)$-alkylphenyl, chlorophenyl, dichlorophenyl, $(C_1-C_6)$-alkoxyphenyl, $\alpha$- or $\beta$-naphthyl, or a group of the formula $-(CH_2CH_2O)_n-R$ in which n is 1 or 2 or 3 and R stands for hydrogen, $(C_1-C_7)$-alkyl, $(C_1-C_4)$-alkylmercapto-$(C_1-C_4)$-alkyl, dimethyl- or diethyl-amino-$(C_1-C_4)$-alkyl, or morpholino-$(C_1-C_4)$-alkyl, are of special interest.

Further preferred compounds of formula I are those in which X is O or S, $R_1$ and $R_2$, which are in 5- and 7-position, are hydrogen or chlorine, $(C_1-C_4)$-alkyl, phenyl, or together form a fused phenyl ring, and $R_3$ in group A means $(C_1-C_6)$-alkyl, $(C_1-C_6)$-chloroalkyl, $(C_1-C_4)$-alkoxy-$(C_1-C_4)$-alkyl, hydroxy-$(C_1-C_4)$-alkyl, or a group of the formula $-(CH_2CH_2O)_n-R'$ in which n is 2 or 3 and R' stands for hydrogen or $(C_1-C_4)$-alkyl.

A further sub-class of preferred compounds of formula I includes those in which X is oxygen, $R_1$ in 5-position is hydrogen or chlorine, methyl or phenyl, $R_2$ represents hydrogen, or $R_1$ and $R_2$ are methyl either in 5,6-position or in 5,7-position, and $R_3$ in group A represents methyl, ethyl, n- or i-propyl, n- or i-butyl, pentyl, chloromethyl, $\beta$-chloroethyl, $\beta$-hydroxyethyl, $\beta$-methoxyethyl-, $\beta$-ethoxyethyl, benzyl, phenyl, o-tolyl, p-tolyl, 2,4-dimethylphenyl, o-chlorophenyl, p-chlorophenyl, 2,4-dichlorophenyl, or p-methoxyphenyl.

Besides the aforesaid sub-groups, other sub-groups may be formed with the individual meanings for the symbols X, $R_1$, $R_2$, A and $R_3$. It has to be understood that the formation of such novel sub-groups does not mean to introduce new matter according to 35 U.S.C. 132.

The term "functionally modified carboxy or sulfo groups" is intended to include:

cyano, carboxylic acid ester, carboxylic acid amide, mono- and di-alkylcarbamide, sulfonic acid ester, and mono- and dialkyl-sulfonamide groups.

More particularly, suitable radicals $R_1$ and $R_2$ are, for example, methyl, ethyl, n- or i-propyl, n- or i-butyl, pentyl, hexyl, methoxy, ethoxy, propoxy, butoxy, pentoxy, hexoxy, dimethylamino, diethylamino, trimethylammonium, triethylammonium, acetylamino, cyano, $-SO_3H$, carboxyl, carbomethoxy, -ethoxy, -propoxy, -butoxy, and the corresponding groups of the series of sulfonic acid alkyl ester groups, methyl-, ethyl-, propyl- and butyl-carboamide and the corresponding groups of the series of alkylsulfonamides and the corresponding dialkylcarbamide or -sulfonamide groups. Two adjacent radicals $R_1$ and $R_2$ may also form together a fused phenyl or cyclohexyl ring. Among the meanings of X all those radicals containing the benzoxazolyl group (X=O) are preferred.

Suitable radicals for $R_3$ are, inter alia, methyl, ethyl n- or i-propyl, n- or i-butyl, pentyl, hexyl, or the chloroalkyl, hydroxyalkyl, dimethylaminoalkyl, diethylaminoalkyl, methoxyalkyl, ethoxyalkyl, propoxyalkyl, butoxyalkyl, methylmercaptoalkyl, ethylmercaptoalkyl, chlorophenoxyalkyl, phenoxyalkyl, phenylmercaptoalkyl, phenylalkyl, naphthylalkyl groups deriving there from; furthermore groups of the formula $-(CH_2CH_2O)_n$ in which n is 1 or 2 or 3 and R stands for hydrogen, methyl, ethyl, propyl, or butyl, dimethyl- or diethylaminoalkoxyalkyl having from 1 to 4 carbon atoms in the alkyl and alkoxy moiety, respectively, or alkylthioalkoxyalkyl groups likewise containing 1 to 4 carbon atoms in the individual alkyl and alkoxy moieties, for example radicals of the formulae —CH$_2$CH$_2$OCH$_3$, —CH$_2$CH$_2$OC$_2$H$_5$,
—CH$_2$CH$_2$OC$_3$H$_7$, —CH$_2$CH$_2$OC$_4$H$_9$,
—CH$_2$CH$_2$OC$_6$H$_{13}$,

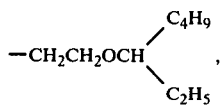

—CH$_2$CH$_2$OC$_6$H$_{11}$, —(CH$_2$CH$_2$O)$_2$CH$_3$, —(CH$_2$CH$_2$O)$_2$C$_2$H$_5$, —(CH$_2$CH$_2$O)$_2$C$_4$H$_9$, —(CH$_2$CH$_2$O)$_3$C$_2$H$_5$, —CH$_2$CH$_2$OCH$_2$CH$_2$SC$_2$H$_5$, —CH$_2$CH$_2$OCH$_2$CH$_2$—N(CH$_2$)$_2$, —CH$_2$CH$_2$OCH$_2$CH$_2$—N(C$_2$H$_5$)$_2$ or

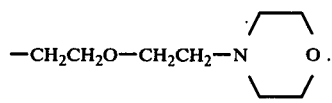

R$_3$ can also stand for an unsubstituted or a mono- or di-substituted phenyl group in which the alkyl, alkoxy, acyl, carbalkoxy, alkylcarbamide, alkylsulfonamide and sulfonic acid alkyl ester groups may contain from 1 to 4 carbon atoms. Two substituents R$_4$ and R$_5$ together may also from a fused phenyl or cyclohexyl ring.

The invention also provides a process for preparing compounds of formula I, which comprises reacting a compound of the formula II

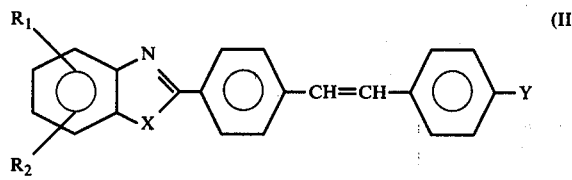

with a compound of the formula III

R$_3$ - Z          (III)

in which R$_1$, R$_2$, X and R$_3$ have the aforesaid meanings and Y represents a group of the formula IV

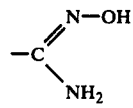          (IV)

and Z stands for a group of the formula V

—COCl          (V), or Y represents a group of formula V and Z represents a group of formula IV.

In the former case, compounds of formula I are obtained containing a 1,2,4-dioxazolyl-3 group and in the latter case the compounds obtained contain the 1,2,4-dioxazolyl-5 group.

The reaction is preferably carried out in the presence of an acid-binding agent in an inert solvent at a temperature of from 20° to 200° C. Suitable solvents for the reaction are, for example, chlorobenzene, di- and trichlorobenzene and especially dimethylformamide, N-methylpyrrolidone, dimethylsulfoxide and nitrobenzene. As acid-binding agent sodium carbonate, calcium carbonate, potassium carbonate, triethylamine or ethyldiisopropylamine may be used.

The compounds of formula II in which Y is a group of formula IV are obtained by reacting the corresponding nitriles with hydroxyl amine, preferably in an alcohol or N-methylpyrrolidone. The corresponding nitriles are described in literature and can be prepared by known processes (cf. JA-Sho-42-21013, U.S. Pat. No. 3,577,411, DT-OS 2,000,027). Benzoxazolyl-stilbene-carboxylic acid carrying appropriate substituents can be transformed, for example, in known manner, via the acid chloride into the amide which is then reacted with an agent splitting off water to obtain the nitrile. The starting compounds of formula II in which Y stand for a group of formula IV can be prepared by the process described in Chem. Rev. 62 (1962), pages 155 et seq.. The starting compounds of formula III in which Z stands for a group of formula IV can be prepared in analogous manner by the same process. The starting compounds of formula II in which Y represents a group of the formula V are obtained by the following reaction stages known to the expert:

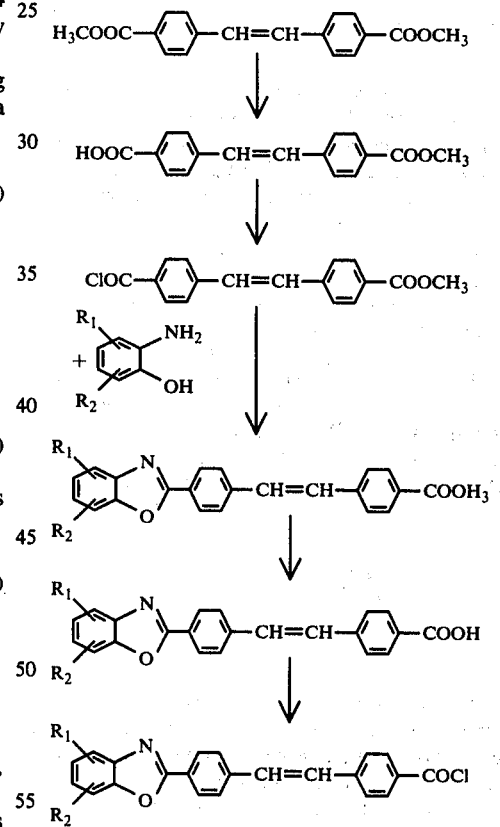

The reaction products obtained by the aforesaid processes can by further transformed in known manner, for example the sulfo- or carboxy-containing molecules can be transformed into functionally modified sulfo- or carboxy groups, or groups of this type can be transformed into other corresponding groups or into the free acids. In known manner chloromethyl groups can be introduced or methyl groups can be oxydized. Halogenations are also possible as well as further reactions with introduced halogen atoms, for example the exchange of chlorine or bromine for the amine function.

The novel compounds of formula I are almost colorless, fluorescent substances which can be used as optical brighteners.

Substances which can be brightened with the use of the compounds of the invention are, for example: lacquers, natural and synthetic fibers, for example those of natural or regenerated cellulose, acetyl cellulose, natural and synthetic polyamides, such as wool, polyamide-6 and -6,6, polyesters, polyolefins, polyvinyl chloride, polyvinylidene chloride, polystyrene, or polyacrylonitrile, as well as sheets, films, ribbons or other shaped structures of these materials.

The compounds of the invention, which are insoluble in water, can be used in the form of solutions in organic solvents or in aqueous dispersion, preferably with the addition of a dispersant, for example soaps, polyglycol ethers deriving from fatty alcohols, fatty amines, or alkyl phenols, sulfite cellulose liquor, or condensation products of optionally alkylated naphthalene-sulfonic acids with formaldehyde.

Compounds of formula I can also be added to detergents which may contain the usual fillers and auxiliaries such as alkali metal silicates, alkali metal phosphates and polymetaphosphates, alkali metal borates, alkali metal salts of carboxymethyl cellulose; foam stabilizers such as alkanol amides of higher fatty acids, or complex forming agents, such as soluble salts of ethylene-diamine tetraacetic acid or diethylenetriamine pentaacetic acid, as well as chemical bleaching agents, such as perborates or percarbonates.

To brighten the fiber material with the aqueous or possibly organic brightening bath there is used either the exhaustion process, which is carried out at a temperature preferably of from about 20° C. to about 150° C., or the thermosol process in which the textile material is impregnated or sprayed with the solution or dispersion of the brightener, squeezed between rolls to a residual moisture content of about 50 to 120% and then subjected to a thermal treatment for about 10 to 300 seconds, preferably with dry heat of about 120° to 240° C. This thermosol process can also be combined with other finishing operations, for example finishing with artificial resins to obtain easy-care properties.

Alternatively, the compounds of the invention can be added to high molecular weight organic substances prior to or during shaping, for example in the manufacture of films, sheets, ribbons, or shaped structures to the masses to be moulded, or prior to spinning they can be dissolved in the spinning mass. Suitable compounds can be added prior to polycondensation or polymerization, to the low molecular weight compounds for example in the case of polyamide-6, polyamide-6,6, or linear esters of the type of polyethylene glycol terephthalate.

Compounds of the invention substituted by one and preferably two carboxy or carbalkoxy groups can be bound to linear polyester molecules and synthetic polyamides by an ester or amide linkage by adding them to these materials or preferably to the starting compounds under suitable conditions. In this case, the brighteners are anchored by a chemical bond in the substratum and are then characterized by a much higher stability to sublimation and to solvent.

The amount of compounds I to be added to the material to be brightened can vary within wide limits depending on the intended application and the desired effect. It can be easily determined by preliminary tests and, in general, it is in the range of from about 0.01 and about 2%, calculated on the material.

The following examples illustrate the invention, the parts and percentages being by weight unless otherwise stated.

EXAMPLE 1

18 parts of 4'-benzoxazolyl-2-stilbene-4-carboxylic acid chloride and 6.8 parts of benzamidoxime in 300 parts of o-di-chlorobenzene were refluxed while stirring for 7 hours.

The icecold reaction mixture was filtered off with suction and the residue washed with o-dichlorobenzene and methanol. After drying, 15.1 parts (68.4% of the theory) of 3-(4'-benzoxazolyl-2-stilbenyl-4")-5-phenyl-1,2,4-oxdiazole

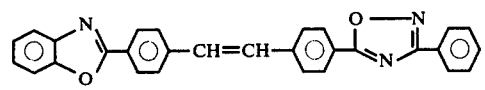

were obtained which melted at 250° to 252° C. after recrystallization from dioxane Absorption: (in DMF) $\lambda_{max} = 367$ nm; $\epsilon = 77\,700$.

EXAMPLE 2

Under the conditions specified in Example 1, 16.5 parts (72.3%) of the compound of the formula

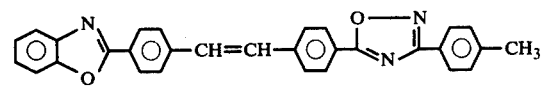

were obtained using 7.5 parts of p-tolyamidoxime.

EXAMPLE 3

18 parts of 4'-benzoxazolyl-2-stilbene-4-carboxylic acid chloride and 5 parts of tiethyl-amine were added to 7.5 parts of o-tolylamidoxime in 150 parts of N-methyl-pyrrolidone and the whole was stirred for 1 hour at room temperature. The mixture was then heated to 160° to 170° C., stirring was continued for 15 minutes, cooled and the icecold mixture was filtered off with suction and washed with methanol. 16.2 parts (71% of the theory) of the compound of the formula

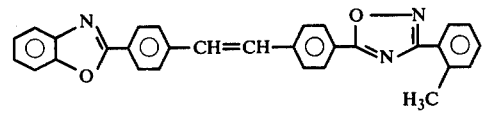

were obtained, which after recrystallization from o-dichlorobenzene/bleaching earth had the following melting properties: it sintered at 222° C., showed a liquid-crystalline transition at 229° to 232° C. and melted at 293° C.

Absorption: (in DMF) $\lambda_{max} = 367$ nm; $\epsilon = 70\,200$.

EXAMPLE 4

Using 9.3 parts of 2-naphthylamidoxime unter the conditions specified in Example 3 there were obtained 20.2 parts (82% of the theory) of the compound of the formula

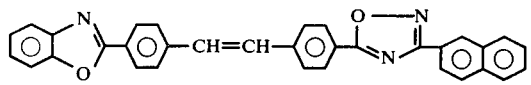

which, after recrystallization from dimethylformamide/animal charcoal, had the following melting properties: it sintered at 242° C., showed a liquid-crystalline transition at 243° to 268° C. and melted above 300° C.

Absorption: (in DMF) $\lambda_{max} = 366$ nm; $\epsilon = 75\,500$.

EXAMPLE 5

Using 7.5 parts of benzylamidoxime under the conditions of Example 3 there were obtained 16.8 parts (74% of the theory) of the compound of the formula

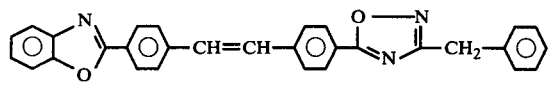

which, after recrystallization from dimethylformamide/animal charcoal, had the following melting properties: it sintered at 225° C., showed a liquid-crystalline transition at 237° to 242° C. and melted at 249° C.

Absorption: (in DMF) $\lambda_{max} = 366$ nm; $\epsilon = 64\,700$.

EXAMPLE 6

Using 3.7 parts of acetamidoxime under the conditions of Example 3 there were obtained 13.8 parts (73% of the theory) of the compound of the formula

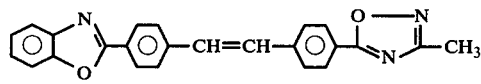

which, after recrystallization from dimethylformamide/animal charcoal, had the following melting properties: it sintered at 195° C., showed a liquid-crystalline transition at 217° to 225° C. and melted at 264° C.

Absorption: (in DMF) $\lambda_{max} = 363$ nm; $\epsilon = 65\,400$.

EXAMPLE 7

Using 5.5 parts of chloroacetamidoxime under the conditions of Example 3 there were obtained 9.9 parts (48% of the theory) of the compound of the formula

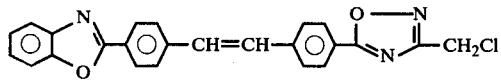

which, after recrystallization from methyl glycol/animal charcoal, had the following melting properties: is sintered at 205° C., it showed a liquid-crystalline transition at 240° to 244° C. and had a decomposition point of about 300° C.

EXAMPLE 8

Using 8.3 parts of 4-methoxybenzamidoxime unter the conditions of Example 3 there were obtained 14.3 parts (62% of the theory) of the compound of the formula

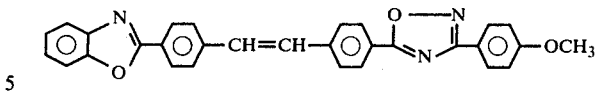

which, after recrystallization from dimethylformamide/animal charcoal, had the following melting properties: it sintered at 229° C., showed a liquid-crystalline transition at 270° to 280° C. and melted above 300° C.

Adsorption: (in DMF) $\lambda_{max} = 368$ nm; $\epsilon = 76\,700$.

EXAMPLE 9

Using 8.3 parts of 3-oxypropionic amidoxime under the conditions of Example 3 there were obtained 13.0 parts (55% of the theory) of the compound of the formula

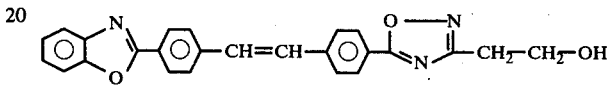

which, after recrystallization from dimethylformamide/animal charcoal, had the following melting properties: it sintered at 211° C., showed a liquid-crystalline transition at 215° to 221° C. and melted at 280° C. with decomposition.

Absorption: (in DMF) $\lambda_{max} = 368$ nm; $\epsilon = 76\,700$.

EXAMPLE 10

Using 8.5 parts of 4-chlorobenzamidoxime under the conditions of Example 3 there were obtained 16.2 parts (68% of the theory) of the compound of the formula

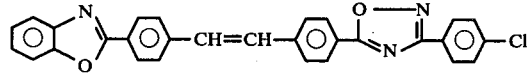

which, after recrystallization from dimethylformamide/animal charcoal, had the following melting properties: it sintered at 225° C., showed a liquid-crystalline transition at 230° to 234° C. and it melted above 300° C.

Absorption: (in DMF) $\lambda_{max} = 367$ nm; $\epsilon = 67\,100$.

EXAMPLE 11

Using 9.3 parts of 1-naphthylamidoxime under the conditions of Example 3 there were obtained 16.0 parts (65% of the theory) of the compound of the formula

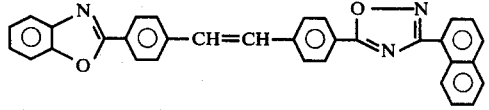

which, after recrystallization from dimethylformamide/animal charcoal, had the following melting properties: it sintered at 233° C., showed a liquid-crystalline transition at 260° to 261° C. and melted above 300° C.

Absorption: (in DMF) $\lambda_{max} = 368$ nm; $\epsilon = 69\,700$.

EXAMPLE 12a 171 g of 4'-benzoxazolyl-2-stilbene-carboxylic acid in 1,500 ml of toluene, 428 g of thionyl chloride and 1 g of dimethylformamide were refluxed for 5 hours, the excess thionyl chloride was distilled off with the toluene, the contents of the reaction flask were cooled to 30° C. and ammonia was introduced until saturation. Introduction of ammonia was continued while refluxing for a further 2 hours, the reaction mixture was cooled, washed and dried.

146 g (86% of the theory) of 4'-benzoxazolyl-2-stilbene-carboxylic acid amide of the formula

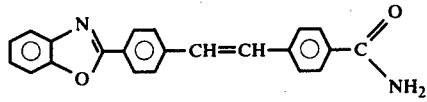

were obtained which, without purification, was refluxed while stirring in a mixture of 1,400 g of thionyl chloride and 5 g of DMF. The thionyl chloride was distilled off until the residue was dry, the residue was stirred with water, filtered off with suction, washed until neutral and dried. 131 g (95% of the theory) of 4'-benzoxazolyl-2-stilbene-carboxylic acid nitrile of the formula

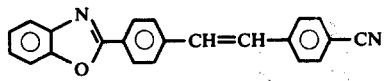

were obtained which, after recrystallization from methyl glycol and animal charcoal, melted at 240° to 242° C.

IR: $\nu C{\equiv}N$ 2222 cm$^{-1}$ UV: $\lambda_{max}$ = 358 nm $\epsilon$ = 7.1×10$^4$

EXAMPLE 12b 7.4 g of hydroxylamine hydrochloride and 50 ml of n-butanol were mixed while stirring at 70° C. A little phenophthalein was added and a solution of 5.0 g of sodium methylate in 50 ml of n-butanol was added at a rate such that the red color of the phenolphthalein disappeared at once. The mixture was allowed to cool, filtered to separate the sodium chloride and washed with 20 ml of n-butanol. 14.6 g of 4'-benzoxazolyl-2-stilbene-carboxylic acid nitrile were added to the filtrate and the mixture was stirred for 48 hours at 80° C. The cold reaction mixture was filtered off with suction, washed with n-butanol and dried. 15.2 g (94.6% of the theory) of 4'-benzoxazolyl-2-stilbene-4-amidoxime of the formula

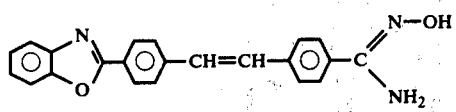

were obtained in the form of a light yellow powder. The crude product melted at 270° to 271° C. with decomposition. It could be further used without purification.

EXAMPLE 12c 3.6 g of 4'-benzoxazolyl-2-stilbene-4-amidoxime are mixed while stirring with 40 ml of dimethylformamide and 0.9 g of acetyl chloride and 1.3 g of triethylamine were added. The mixture was stirred for 1 hour at room temperature, rapidly cooled and then refluxed for 30 minutes and cooled again. After cooling, the mixture was filtered with suction and washed with a little dimethylformamide and methanol. After drying, 2.4 g (63.3 g of the theory) of 3-[4'-benzoxazolyl-2-stilbene-4]-5-methyl-1,2,4-oxidazole of the formula

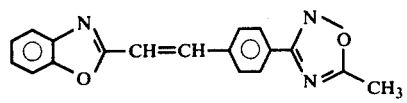

were obtained which, after recrystallization from dimethylformamide while clarifying with animal charcoal, showed a crystalline-liquid transition at 259° C. to 263° C. and melted at 333° C.

EXAMPLE 13

Instead of acetyl chloride as in Example 12c, 2.1 g of 2,4-dichlorobenzoyl chloride were used and 3.6 g (71% of the theory) of 3-(4'-benzoxazolyl-stilbenyl-4-)-5-(2,4-dichlorophenyl)-1,2,4-oxidazole of the formula

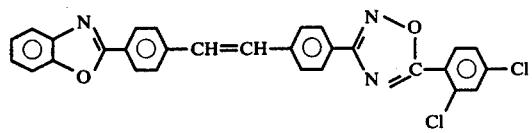

were obtained, which after recrystallization from dimethylformamide while clarifying with animal charcoal, had a crystalline-liquid transition at 210°–214° C. and melted at 245° C.

The compounds listed in the following tables were prepared in analogous manner.

| R = | | melting properties |
|---|---|---|
|  | sintered at<br>liquid crystalline transition | 235–239° C<br>241–247° C |
| | melting point | 325° C |
| —OCH$_3$ | sintered at<br>liquid crystalline transition | 214° C<br>255–275° C |
| | melting point | 323° C |
| | sintered at<br>liquid crystalline transition | 229° C<br>230–231° C |
| R = —CH$_2$—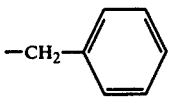 | melting point | 256–258° C |
| | sintered at<br>liquid crystalline transition | 212° C<br>265–276° C |
| R = —CH$_2$—CH$_3$ | melting point<br>sintered at<br>liquid crystalline transition | 317° C<br>213° C<br>249–258° C |
| R = —CH=CH—CH$_3$ | melting point<br>sintered at<br>crystalline transition | 263° C<br>225° C<br>230–235$^5$C |
| R = —CH$_2$Cl | melting point | 237° C |

Structure:

$R_1, R_2$-substituted benzoxazole—CH=CH—C₆H₄—CH=CH—C₆H₄—(oxazole with $R_3$)

| Ex. No. | $R_3$ | $R_1, R_2$ | yield [% of theory] | sintered | liquid crystalline transition | melting point | λ max [nm] | absorption (in DMF) ε |
|---|---|---|---|---|---|---|---|---|
| 14 | —CH₂—N(CH₃)₂ | H | 76 | 212 | 228–229 | 261 | — | — |
| 15 | m-tolyl (CH₃-phenyl) | H | 73 | 222 | 242–254 | >300 | 367 | 74 000 |
| 16 | —CH₂—CH₂—OCH₃ | H | 75 | — | 218 | 220–221 | 366 | 67 200 |
| 17 | —CH₂—CH₃ | H | 79 | 223 | 258–275 | >300 | 366 | 72 000 |
| 18 | —CH₃ | $R_5$=—Cl | 65 | 294 | 313–320 | 325 | 367 | 64 200 |
| 19 | —CH₃ | $R_5$=—CH₃ | 72 | 212 | 226–241 | 272 | 366 | 69 300 |
| 20 | —CH₃ | $R_5$=phenyl | 75 | — | 260–264 | >300 | 368 | 76 200 |
| 21 | —CH₃ | $R_5, R_7$=—CH₃ | 68 | 230 | 232–234 | 296–300 | — | — |
| 22 | —CH₂—CH₃ | $R_5, R_6$=—CH₃ | 65 | — | 205–210 | 215 | — | 75 300 |
| 23 | —CH₂—CH₂—O—CH₃ | $R_5, R_6$=—CH₃ | 67 | — | 265–267 ~300 | — | 366 | — |
| 24 | —CH₃ (H₃C, H₃C substituted benzoxazole) | — | 82 | — | 268–271 ~320 | — | 367 | 69 500 |
| 25 | (phenyl-substituted oxazole system) | — | 82,5 | — | 275–276 ~330(Z)* | — | — | — |
| 26 | (benzothiazole system, CH₃-oxazole) | — | — | 225° C | 246–250° C | 300° C | 364 | 65 200 |

*proper melting point

What is claimed is:

1. A compound of the formula I

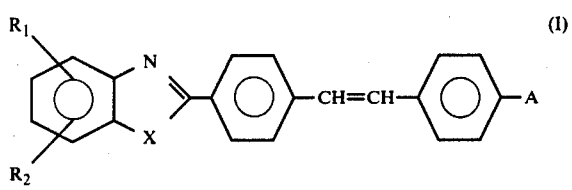

in which X is O or S, $R_1$ and $R_2$, which can be identical or different, are selected from hydrogen, fluorine, chlorine, phenyl, lower alkyl, lower alkoxy, lower dialkylamino, lower trialkylammonium, acylamino and optionally functionally modified carboxy or sulfo radicals, two adjacent radicals $R_1$ and $R_2$ together possibly represent phenylene, lower alkylene or 1,3-dioxapropylene and A represents a group of the formula

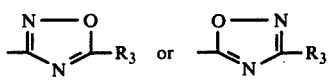

in which $R_3$ represents a straight chain or branched alkyl radical having from 1 to 18 carbon atoms, preferably 1 to 6 carbon atoms, which may be substituted by hydroxy, halogen, lower alkoxy, lower dialkylamino, lower alkylmercapto, chloroaryloxy, aryloxy, arylmercapto, or aryl, in the case of dialkylaminoalkyl the two alkyl groups together possibly forming a morpholine, piperidine or piperazine ring, or $R_3$ represents a group of the formula $-(CH_2CH_2O)_n-R$, wherein n is 1, 2, or 3 and R is hydrogen, lower alkyl, dialkylaminoalkoxyalkyl or alkylthioalkoxyalkyl, the alkyl radicals in the dialkylaminoalkoxyalkyl possibly forming together a piperidine, hexamethylene-imine, morpholine or piperazine ring, or $R_3$ stands for a group of the formula $-(CH_2)_m-CH=CH-R$ with m being zero or in the range of from 1 to 5, or a radical of the formula

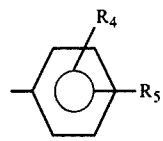

in which $R_4$ and $R_5$, which can be identical or different, are selected from the group of hydrogen, fluorine, chlorine, phenyl, lower alkyl, lower alkoxy, $(C_1-C_4)$-acylamino, or possibly modified carboxy or sulfo groups, two adjacent radicals $R_4$ and $R_5$ possibly representing together a lower alkylene group, a fused benzene ring or a 1,3-dioxapropylene group.

2. A compound as claimed in claim 1 which X, A, $R_1$ and $R_2$ have the meanings indicated in claim and $R_3$ is selected from $(C_1-C_6)$alkyl, $(C_1-C_6)$-chloroalkyl, dimethyl- or diethylamino-$(C_1-C_4)$-alkyl, morpholino-ethyl, N-$\beta$-piperidinoethyl, N-$\beta$-(N'-methylpiperazino)-ethyl, benzyl, phenoxy-$(C_1-C_4)$alkyl, chlorophenoxy-$(C_1-C_4)$-alkyl, $(C_1-C_4)$-alkylmercapto-$(C_1-C_4)$alkyl, phenylmercapto-$(C_1-C_4)$-alkyl, phenyl, $(C_1-C_6)$-alkylphenyl, di-$(C_1-C_6)$-alkylphenyl, chlorophenyl, dichlorophenyl, $(C_1-C_6)$-alkoxyphenyl, - or $\beta$-naphthyl, a group of the formula $-(CH_2CH_2O)_n-R$ in which n is 1 or 2 or 3 and R stands for hydrogen, $(C_1-C_7)$-alkyl, $(C_1-C_4)$-alkylmercapto-$(C_1-C_4)$-alkyl, di-methyl- or diethylamino-$(C_1-C_4)$-alkyl, and morpholino-$(C_1-C_4)$-alkyl.

3. A compound as claimed in claim 1, in which X is O or S, $R_1$ and $R_2$ which are in 5- and 7-position are hydrogen or chlorine, $(C_1-C_4)$-alkyl, phenyl, or together a fused phenyl ring and $R_3$ in group A means $(C_1-C_6)$-alkyl, $(C_1-C_6)$-chloroalkyl, $(C_1-C_4)$-alkoxy-$(C_1-C_4)$-alkyl, hydroxy-$(C_1-C_4)$-alkyl, or a group of the formula $-(CH_2CH_2O)_n-R'$ in which n is 2 or 3 and R' stands for hydrogen or $(C_1-C_4)$-alkyl.

4. A compound as claimed in claim 1 in which X is oxygen, $R_1$ in 5-position is hydrogen or chlorine, methyl or phenyl, $R_2$ represents hydrogen, or $R_1$ and $R_2$ both are methyl groups either in 5,6-position or in 5,7-position, and $R_3$ in group A represents methyl, ethyl, n- or i-propyl, n- or i-butyl, pentyl, chloromethyl, $\beta$-chloroethyl, $\beta$-hydroxyethyl, $\beta$-methoxyethyl-, $\beta$-ethoxyethyl, benzyl, phenyl, o-tolyl, p-tolyl, 2,4-dimethylphenyl, o-chlorophenyl, p-chlorophenyl, 2,4-dichlorophenyl, or p-methoxyphenyl.

* * * * *